US00PP33330P2

(12) United States Plant Patent
Clark

(10) Patent No.: US PP33,330 P2
(45) Date of Patent: Aug. 10, 2021

(54) BLACKBERRY PLANT NAMED 'PONCA'

(50) Latin Name: ***Rubus* subgenus *Rubus* Watson**
Varietal Denomination: Ponca

(71) Applicant: THE BOARD OF TRUSTEES OF THE UNIVERSITY OF ARKANSAS, Little Rock, AR (US)

(72) Inventor: John R. Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/880,798

(22) Filed: May 21, 2020

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
CPC ..... A01H 6/7499
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al. |
| PP11,865 | P2 | 5/2001 | Clark et al. |
| PP14,935 | P2 | 6/2004 | Clark |
| PP15,788 | P2 | 6/2005 | Clark |
| PP16,989 | P3 | 8/2006 | Clark et al. |
| PP17,162 | P3 | 10/2006 | Clark |
| PP17,983 | P2 | 9/2007 | Cabrera Avalos |
| PP20,891 | P3 | 3/2010 | Clark |
| PP22,449 | P3 | 1/2012 | Clark |
| PP23,497 | P3 | 3/2013 | Clark et al. |
| PP24,249 | P3 | 2/2014 | Clark |
| PP25,864 | P3 | 9/2015 | Clark |
| PP26,120 | P3 | 11/2015 | Clark |
| PP26,368 | P3 | 2/2016 | Banados Ortiz et al. |
| PP26,405 | P3 | 2/2016 | Clark et al. |
| PP26,413 | P3 | 2/2016 | Ortiz et al. |
| PP26,990 | P3 | 8/2016 | Clark |
| PP27,032 | P2 | 8/2016 | Clark |
| PP27,401 | P3 | 11/2016 | Clark et al. |
| PP28,598 | P3 | 11/2017 | Clark |

OTHER PUBLICATIONS

U.S. Appl. No. 16/602,884, filed Dec. 18, 2019.
U.S. Appl. No. 16/602,892, filed Dec. 19, 2019.
U.S. Appl. No. 16/873,341, filed Mar. 24, 2020.
U.S. Appl. No. 16/880,780, filed May 21, 2020.
Blaedow, K. et al. Blackberry Advanced Breeding Line Trial: Bringing New Cultivars to NC. Poster presented at 2020 NARBA Conference. Mar. 3-6, 2020. St Louis, MO.
Blaedow, K. et al. Blackberry Advanced Breeding Line Trial: Bringing New Cultivars to NC. Poster presented North Caroline State Annual Extension Conference Oct. 28-Oct. 31, 2019. Raleigh, NC.
Clark, J.R. 2013. 'Osage' thornless blackberry. HortScience 48:909-912.
Clark, J.R. et al. 2008. 'Natchez' thornless blackberry. HortScience 43:1897-1899.
Clark, J.R. et al. 2005. 'Ouachita' thornless blackberry. HortScience 40:258-260.
Clark, J.R. et al. 2011. APF-45 primocane-fruiting blackberry. HortScience 46.4 (2011): 670-673.
Clark, J.R. et al. 2019. 'Caddo' thornless blackberry. Hortscience 54:1632-1636. https://doi.org/10.21273/HORTSCI14119-19.
University of Arkansas. Blackberries—Ponca. Flyer. Nov. 1, 2019.
USDA Plant Hardiness Zone Map. 2013. United States Department of Agriculture—Agricultural Research Service. May 17, 2013. http://planthardiness.ars.usda.gov/PHZMWeb/.

*Primary Examiner* — Anne Marie Grunberg
(74) *Attorney, Agent, or Firm* — Quarles & Brady LLP

(57) ABSTRACT

Description and specifications of a new and distinct cultivar of blackberry plant named 'Ponca' which originated from seed produced by a hand-pollinated cross 'Ark. 2406' (a non-patented, unreleased genotype) x 'Ark. 2253T' (a non-patented, unreleased genotype). This new cultivar of blackberry plant can be distinguished by its medium size, very firm berries with very sweet, sub-acid flavor, excellent postharvest fruit-handling potential, early season ripening, and excellent plant health.

3 Drawing Sheets

Latin name: *Rubus* subgenus *Rubus* Watson.
Varietal denomination: 'Ponca'.

BACKGROUND

The new floricane-fruiting cultivar of blackberry called 'Ponca' is described herein. The new cultivar originated from a hand-pollinated cross of 'Ark. 2406' (a non-patented, unreleased genotype) x 'Ark. 2253T' (a non-patented, unreleased genotype) made in 2008. The seeds resulting from this controlled hybridization were germinated in a greenhouse in the spring of 2009 and planted in a field near Clarksville, Ark. (West-Central Arkansas). The seedlings fruited in the summer of 2012 and one seedling, designated 'A-2538T' now called 'Ponca', was selected for its medium size, very firm berries with very sweet, sub-acid flavor, excellent postharvest fruit-handling potential, early season ripening, and good plant health.

SUMMARY OF THE INVENTION

This new and distinct cultivar of blackberry originated from a hand-pollinated cross of 'Ark. 2406' (a non-patented, unreleased genotype) x 'Ark. 2253T' (a non-patented, unreleased genotype) made in 2008 and located near Clarksville, Ark. (West-Central Arkansas). The botanical designation of the new cultivar of blackberry is *Rubus* L. subgenus *Rubus* Watson. The seeds resulting from this controlled hybridization were germinated in a greenhouse in the winter to early spring of 2009 and planted in a field near Clarksville, Ark. The seedlings fruited in the summer of 2012 on floricanes and one seedling, designated 'A-2538T', now 'Ponca', was selected for medium size, very firm berries with very sweet, sub-acid flavor, excellent postharvest fruit-handling potential, early season ripening, and good plant health.

During 2012, the original plant selection was propagated asexually from root cuttings at the above-noted location, and a test row of 20 plants was established. Subsequently, larger test plantings have been established with asexually multiplied plants at two locations in Arkansas.

The new cultivar has been asexually multiplied annually since 2012 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

BRIEF DESCRIPTION OF THE PHOTOGRAPHS

The accompanying photographs show typical specimens of the new variety in color as nearly true as it is reasonably possible to make in a color illustration of this character. The plants from which the images were taken were three years old.

DETAILED DESCRIPTION OF THE NEW CULTIVAR 'PONCA'

Figure 1:
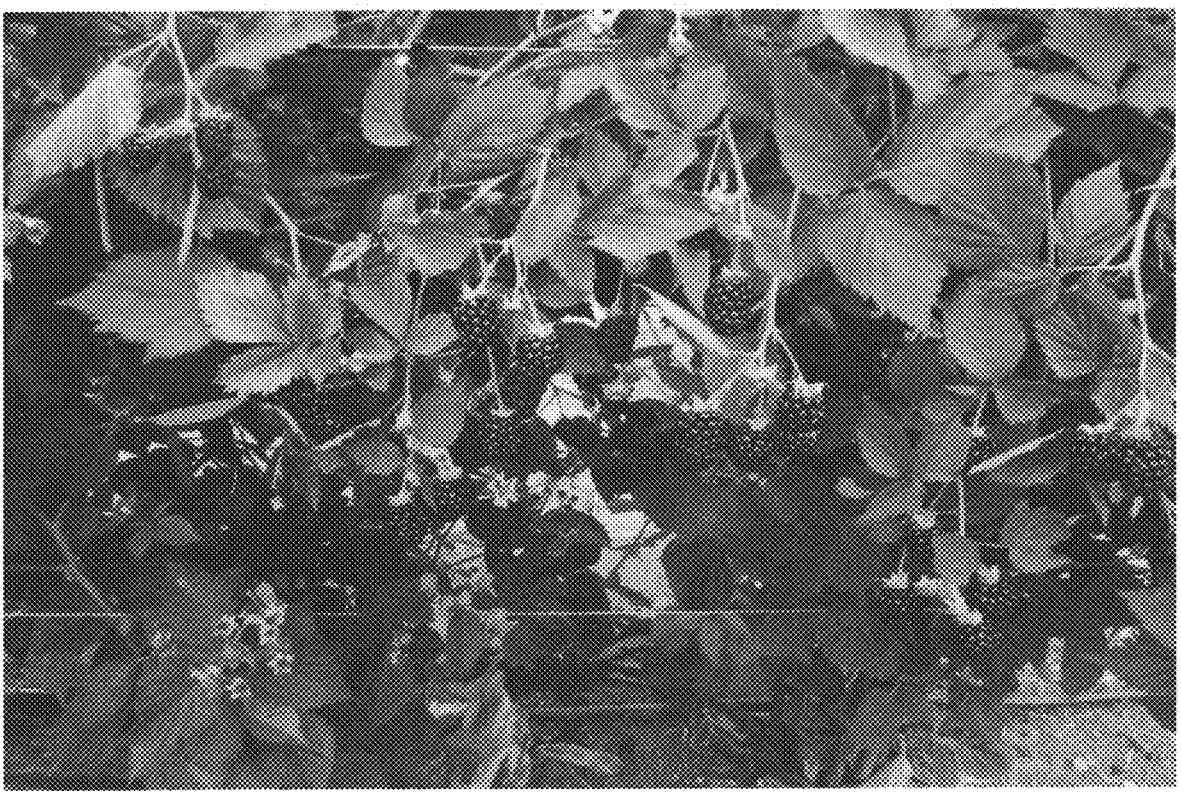
FIG. 1 is a photograph of blackberry canes of 'Ponca' with ripe fruit on the plant.
Figure 2:
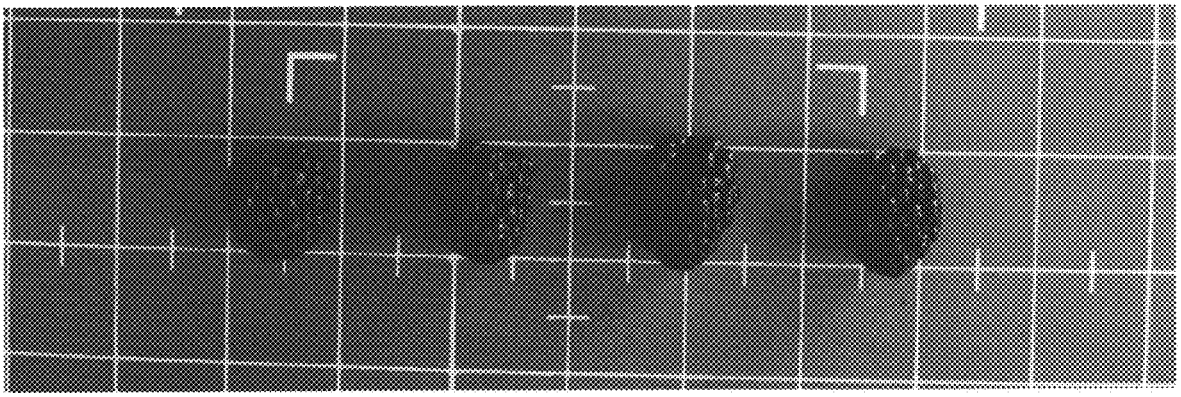
FIG. 2 is a photograph of ripe fruit of 'Ponca'.
Figure 3:
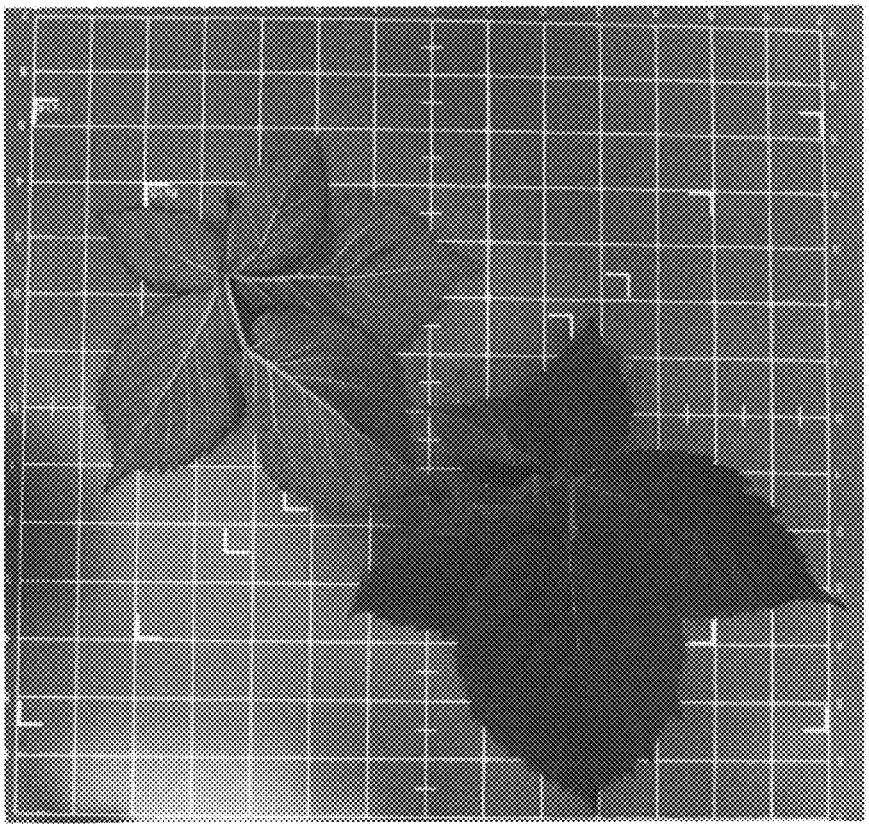
FIG. 3 is a photograph showing the abaxial and adaxial sides of a primocane leaf of 'Ponca'.

Plants and fruit of this new cultivar differ phenotypically from its parents. The new cultivar is thornless, more productive and its fruit size is smaller than its female parent 'Ark. 2406'. The new cultivar is earlier ripening with more erect canes, larger, and has sweeter fruit than its male parent 'Ark. 2253T'. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruit loads. The plants are thornless. Plants and fruit have shown no evidence of anthracnose [*Elsinoe veneta* (Burkh.) Jenkins], and no evidence of susceptibility to orange rust [*Gymnoconia nitens* (Schwein.) F. Kern and H. W. Thurston.]. Plants have shown slight susceptibility to cane and leaf rust (*Kuehneola uredines* (Link) Arthur). No screening has been done for resistance to double blossom/rosette [*Cercosporella rubi* (Wint.) Plakidas].

The bloom period of the new cultivar begins 26 April for 10% bloom is near that of 'Caddo' (U.S. Plant patent application Ser. No. 16/602,892), and four days later than 'Osage' (U.S. Plant Pat. No. 26,120). The average date for 50% bloom is 1 May, which is two days earlier than 'Caddo' and three days later than 'Osage'.

Fruit of the new cultivar has an average first harvest date of 3 June and is two days earlier than 'Caddo' and 'Osage'. The average floricane fruiting period is 55 days.

Fruit yield of the new cultivar on floricanes averages 5.8 kg (12.7 lb)/plant, slightly less than that for 'Osage' and near that of 'Caddo', in West-Central Arkansas. Plants have performed well with no winter injury with winter temperatures of 1° F. (−17° C.).

The fruit is round in shape and glossy with a uniform black finish. The floricane fruit is medium (ave. 6.2 g), slightly larger than 'Osage', and smaller than 'Caddo'. Fruit size of the new cultivar is maintained well throughout the entire harvest season. The new cultivar exhibits excellent fruit fertility with full drupelet set The dry seed weight for the new cultivar averaged 4.04 mg/seed, larger than 'Osage' and similar to 'Caddo'.

The fresh fruit rates very well in flavor and is a noteworthy attribute of the cultivar and is comparable to 'Osage', and 'Caddo'. Consistent flavor was noted at repeated observations of fruit of this cultivar over the years of evaluation including after rain events that can reduce flavor and overall fruit quality. The flavor is sweet and sub-acid. The soluble solids concentration averages 13.4% on shiny black fruit, which is higher than 'Osage', and 'Caddo'. Titratable acidity averages 0.54 g/L (expressed as citric acid) and is lower than that for 'Osage' (0.89 g/L) and 'Caddo' (1.0 g/L). Storage potential of fresh fruit of the new cultivar is good and overall comparable to 'Osage' and 'Caddo'. Fruit and flower clusters are medium-large, cymose, and are mostly borne on the periphery of the plant canopy, providing easy access to harvest. Flower fertility is high and clusters are well filled.

The following is a detailed description of the botanical and pomological characteristics of the subject blackberry. Color data are presented in Royal Horticultural Society Color Chart designations (1986 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with drip irrigation at or near Clarksville, Ark. The plants were fertilized near budbreak (late March on average) with complete or nitrogen fertilizer and had an additional nitrogen fertilizer application in early July. Primocanes were tipped at approximately 1.14 m (45 inches) and grown in a hedgerow training system including a trellis. Weeds were controlled with pre- and post-emergent herbicides supplemented with mechanical weed control activities. A single application of liquid lime sulfur was applied to the plants at budbreak, and two additional fungicide applications were applied: one near bloom and another two weeks later. Insecticides were used for spotted-wing drosophila (*Drosophila suzukii* Matsumura) control during the harvest season. The descriptions reported herein are from specimens grown near Clarksville, Ark.

Plant:

*Size*.—Medium. Plants are grown in a hedgerow and primocanes tipped at approximately 1.14 m; plants in this system range in size from approx. 107-140 cm tall and 91-102 cm wide.

*Growth habit*.—Upright, moderate vigor, canes erect; suckers from the crown and roots.

*Growth rate*.—Floricane first budbreak 25 February. First emergence of primocanes is 14 May and primocanes reach tipping height (107 cm) on 28 May.

Productivity:

*Floricane*.—5.8 kg (12.7 lb)/plant.

*Cold hardiness*.—Hardy to 1° F. (−17° C.). The low temperature of 1° F. was the lowest the cultivar has been exposed to and fruited successfully after this exposure.

Canes: Thornless, erect.

*Floricane* (*dormant or winter cane*).—Cane: diameter: Base 1.64 cm; midpoint 1.38 cm; terminal 1.17 cm. Cross-section of dormant cane: rounded. Internode length: Base 3.41 cm; midpoint 3.81 cm; terminal 2.43 cm. Floricane color: Base greyed-purple group (187A); midpoint greyed-purple group (183A); terminus greyed-purple group (187A).

*Primocane* (*current-season cane; late summer*).—Cane: Diameter: base 1.49 cm; midpoint 1.69 cm; terminal 1.35 cm. Internode length: Base 5.07 cm; midpoint 3.56 cm; terminal 3.45 cm. Average number of new canes per year: 5-6. Primocane color: Base greyed-purple group (183A); midpoint yellow-green group (146A); terminus yellow-green group (146B). Anthocyanin coloration present on floricanes and primocanes with color most prevalent on sun-exposed canes. Thorn density (per 30 cm of cane length): None, this plant is thornless. Glandular hairs on young shoot: Absent or few. Disease resistance: Plants and fruit have shown no evidence of anthracnose and no evidence of susceptibility to orange rust. Plants have shown slight susceptibility to cane and leaf rust. No screening has been done for resistance to double blossom/rosette. Lateral branching after tipping (measured at the end of growing season): Average number of lateral branches: 6; distribution concentrated on the distal portion (top one-third) of the canes.

Foliage:

*Primocane*.—Leaves: Large; mature compound leaf width 18.89 cm; length 21.13 cm; overall shape: palmate. Glossiness: Abaxial: dull, not glossy; adaxial: dull, not glossy. Color: Base abaxial yellow-green group (147A); adaxial green group (138A); midpoint abaxial yellow-green group (147A); adaxial green group (138A); terminal abaxial yellow-green group (147A); adaxial green group (138A). Leaflet: Width 9.24 cm; length 11.40 cm; shape ovate with acute apex and oblique at the base; margin is serrate; serration teeth length is 0.42 cm and width is 0.49 cm; number of leaflets per compound leaf 5; venation pinnate; young leaf abaxial vein color greyed-orange group (177A); young leaf adaxial vein color yellow-green group (146A); mature leaf abaxial leaf vein color yellow-green group (149C); mature leaf adaxial vein color yellow-green group (149B); no terminal lobing on leaflets; terminal leaflet shape in cross-section is V-shaped (wide); undulation of the terminal leaflet margin is absent; terminal leaflet blistering between veins is weak. Petioles: Length: 6.54 cm; color: abaxial yellow-green group (146B); adaxial yellow-green group (146C); diameter 0.44 cm; texture is mostly smooth, exhibiting light pubescence. Petiolules: Length: 3.34 cm; diameter 0.28 cm; color: abaxial yellow-green group (146B) and adaxial green-purple group (184A); texture is light pubescence. Stipules: 2 per leaf; length: 1.99 cm; width: 1.99 cm; texture: pubescence is present on the adaxial surface of primocane stipules, but not on the abaxial surface; shape: overall shape is subulate; apex acuminate; base rounded; margins are smooth; color: abaxial yellow-green group (145B), adaxial color green group (143A).

*Floricane*.—Leaves: Large; mature compound leaf width 13.46 cm; length 14.68 cm; overall shape: trifoliate. Average date of leaf bud burst: 25 February. Glossiness: Abaxial: dull, not glossy; adaxial: dull, not glossy. Color: base abaxial green group (137B); adaxial green group (131A); midpoint abaxial green group (137B); adaxial green group (131A); terminal abaxial green group (137B); adaxial green group (131A). Leaflet: Width 6.00 cm; length 8.78 cm; shape ovate with acute apex and oblique at the base; margin is serrate; serration teeth length is 0.42 cm and width 0.49 cm; number of leaflets per compound leaf 3; venation pinnate; young leaf abaxial vein color yellow-green group (147C); young leaf adaxial vein color yellow-green group (147B); mature leaf abaxial leaf vein color yellow-green group (145B); mature leaf adaxial vein color yellow-green group (145A); no terminal lobing on leaflets; terminal leaflet shape in cross-section is V-shaped (wide); undulation of the terminal leaflet margin is absent; terminal leaflet blistering between veins is weak. Petioles: Length 4.71 cm; color: abaxial side is green group (143C); adaxial surface green group (138A); diameter 0.20 cm; texture smooth, light pubescence present. Petiolules: Length 1.20 cm; diameter 0.15 cm; color: abaxial surface is green group (138B); adaxial surface is yellow-green group (146B); texture smooth with light pubescence. Stipules: 2 per leaf; length 0.15 cm; width: 0.15 cm; texture: pubescence is present on the adaxial surface of primocane stipules, but not on the abaxial surface; shape: overall subulate; apex acuminate; base rounded; margins are smooth; color: abaxial surface green group (138A), adaxial surface green group (141B).

Flowers:

*Floricane* (*primocances do not produce flowers*).—Date of bloom: First bloom: 26 April; 50% bloom 1 May. Reproductive organs: Stamens — erect, numerous. Pistils — numerous. Pollen — normal, fertile, and abundant. Flower: Diameter: 4.16 cm; depth: 1.80 cm; shape: overall rotate; symmetry: actinomorphic. Petals: Number per flower: 5; length 2.18 cm; width 1.24 cm; shape: apex: rounded; margin: entire (smooth); base: cuneate; color: abaxial surface white group (155C) with greyed-purple group (186D); adaxial surface white group (155C) with greyed-purple group (186D); texture: abaxial: smooth, no pubescence; adaxial: smooth, no pubescence. Flowers per cluster: 7. Sepal: Number per flower: 5;

length 1.06 cm; width: 0.54 cm; shape: overall: lanceolate; apex: acuminate; margin: entire (smooth); base: truncate; texture: abaxial: moderate to heavy pubescence; adaxial: moderate to heavy pubescence; color: abaxial: yellow-green group (144A); adaxial: yellow-green group (146D). Pedicel: Length: 4.00 cm; color: green group (137C); texture: heavy pubescence. Peduncle: Length: 4.24 cm; width: 0.38 cm; color: yellow-green group (146B). Cyme: Type: elongated simple cyme; length: 10.38 cm.

Fruit:

*Maturity*.—Average first ripe date 3 June; Average fruiting period 55 days.

*Size*.—Medium, ave. 6.2 g.

*Primocanes*.—Do not produce fruit.

*Diameter of fruit at primary position on inflorescence*.—Equator 2.02 cm; base pole 1.55 cm; terminal pole 1.93 cm.

*Diameter of fruit at secondary positions on inflorescence*.—Equator 1.85 cm; base pole 1.46 cm; terminal pole 1.73 cm.

*Primary fruit*.—Length: 2.43 cm; shape: round; color: black group (202A).

*Drupelet size*.—0.53 cm.

*Drupelet number per fruit*.—67.

*Seed*.—Average length 0.31 cm; width 0.21 cm; dry weight 4.04 mg; wet weight 5.20 mg; color wet orange-red group (34B); color dry red-purple group (59C).

*Soluble solids*.—13.4%.

*pH*.—3.83.

*Titratable acidity*.—0.54 g/L expressed as citric acid.

*Processed quality*.—Not evaluated for processing.

*Uses*.—Commercial cultivar with excellent potential for shipping, as well as an option for local-market production as well as home gardens.

The cultivar: The most distinctive features of the cultivar are medium size, very firm berries with very sweet, subacid flavor, excellent postharvest fruit-handling potential, early season ripening, and excellent plant health.

I claim:

1. A new and distinct cultivar of blackberry plant named 'Ponca' substantially as illustrated and described herein.

* * * * *